United States Patent
Chavan et al.

(10) Patent No.: US 6,350,912 B1
(45) Date of Patent: Feb. 26, 2002

(54) ONE POT PROCESS FOR THE PREPARATION OF 1-[2-DIMETHYLAMINO-(4-METHOXYPHENYL)-ETHYL] CYCLOHEXANOL

(75) Inventors: Subhash Prataprao Chavan; Subhash Krishnaji Kamat; Latha Sivadasan; Kamalam Balakrishnan; Dushant Anandrao Khobragade; Ravindranathan Thottapillil; Mukund Keshao Gurjar; Uttam Ramrao Kalkote, all of Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/796,082

(22) Filed: Feb. 28, 2001

(51) Int. Cl.[7] ............................................. C07C 211/00
(52) U.S. Cl. ...................................................... 564/336
(58) Field of Search ......................................... 564/336

(56) References Cited

U.S. PATENT DOCUMENTS 2,462,736 A   2/1949   Gresham ..................... 260/584

FOREIGN PATENT DOCUMENTS

EP   0 112 669   7/1984

OTHER PUBLICATIONS

Yardley et al., Journal of Medicinal Chemistry, 1990, 33(10):2899–2905.
Fristad et al., J. Org. Chem., 1985, 50(17):3143–3148.

Primary Examiner—Samuel Barts
(74) Attorney, Agent, or Firm—Darby & Darby

(57) ABSTRACT

A process for the preparation of 2-[dimethylamino-(4-methoxyphenyl)ethyl]-cyclohexanol of formula 1 by reducing 1-[cyano(4-methoxyphenyl)-methyl]cyclohexanol of formula 2

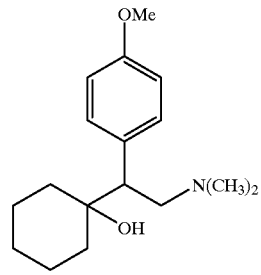

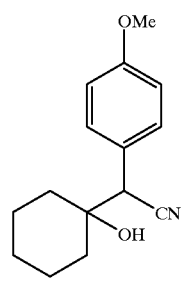

with a formylating agent in a protic solvent in the presence of a catalyst, removing the catalyst by filtration, isolating and purifying the compound of formula 1 is disclosed.

8 Claims, No Drawings

ONE POT PROCESS FOR THE PREPARATION OF 1-[2-DIMETHYLAMINO-(4-METHOXYPHENYL)-ETHYL] CYCLOHEXANOL

FIELD OF THE INVENTION

The present invention relates to a one pot process for the preparation of 1-[2-dimethylamino-(4-methoxyphenyl) ethyl]cyclohexanol of formula 1. 1-[2-dimethylamino-(4-methoxyphenyl)ethyl]cyclohexanol of formula 1 is commonly known as Venlafaxine and also as effexor. More particularly, the present invention relates to a one pot synthesis of compound of formula 1 from 1[Cyano(4-methoxyphenyl)methyl]-cyclo-hexanol having formula 2 which is in turn prepared by a single step conversion comprising the condensation of 4-methoxyphenylacetonitrile with cyclohexanone in the presence of a convenient base like sodium hydroxide.

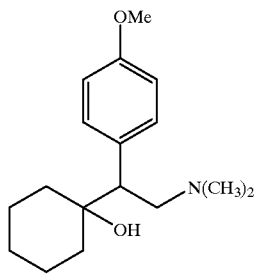

1

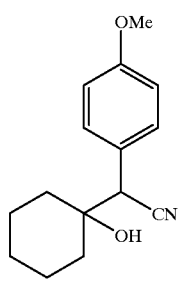

2

BACKGROUND OF THE INVENTION

Venlafaxine having formula 1 and its pharmaceutically acceptable salts thereof are important antidepressants of the central nervous system developed by Wyeth-Ayerat & Company in 1993 [Zhou Jinpei, Zhang Huibin, Huang Xuezhe Huang Wenlong J, China Pharm. Univ. 1999, 30(4) P.249–50].

In the prior art [Husbands et al. U.S. Pat. No. 4,535,186 (1985)] compound of the formula 1 is prepared by reaction of p-methoxy phenyl acetonitrile at −78° C., with cyclohexanone under the influence of n-butyl lithium, following available methods [Sauvetre et al. Tetrahedron 34 2135 (1978)] followed by reduction under high pressure using Rhodium on alumina as the catalyst obtained through Lou-c-kart reaction. Symmetrical N-methylation is accomplished via modified Eschweiler-Clarkes procedure employing formalin, formic acid and a large excess of water as illustrated by Tilford et all [J.A.C.S. 76, 2431 (1954)]. Alternatively, the procedure of Borch and Hassid using sodium cyano borohydride and formaldehyde is employed.

In another prior art [Robin Gerald Shepherd UK Patent No GB 2 227 743 A (1990)] the condensation of 4-methoxyphenylacetonitrile with cyclohexanone is accomplished by the use of lithiumdiisopropylamide in hydrocarbon solvents like hexane toluene or cyclohexane at ambient temperature thereby improving the yield to 79% and further reduction of 2 to the amine followed by protection of the amine to the required compound of formula 1.

In yet another prior art [Zhou Jinpei, Zhang Huibin, Huang Xuezhen, Huang Wenlong J, China Pharm. Univ. 1999, 30(4) P.249–50], anisole is acylated to the chloroacetyl derivative and aminated using N,N Dimethylamine, the carbonyl group of this compound reduced to alcohol using $KBH_4$ and converted to the bromo derivative using $PBr_3$ which in turn when reacted with Mg and then cyclohexanone underwent a Grignard reaction to provide Venlafaxine.

The use of reagents like butyllithium and lithiumdiisopropylamide, Rhodium on alumina and chloroacetylchloride poses severe drawbacks because of their hazardous nature. More over the solvents used are also hazardous and inconvenient in the large-scale preparation of compound of formula 1.

OBJECTS OF THE INVENTION

The object of the present invention is to provide a simple and convenient method of synthesis of venlafaxine using easily available raw materials.

SUMMARY OF THE INVENTION

Accordingly, the present invention relates to a process for the preparation of 2-[dimethylamino-(4-methoxyphenyl) ethyl]-cyclohexanol of formula 1 which comprises reducing 1-[cyano(4-methoxyphenyl)-methyl] cyclohexanol of formula 2

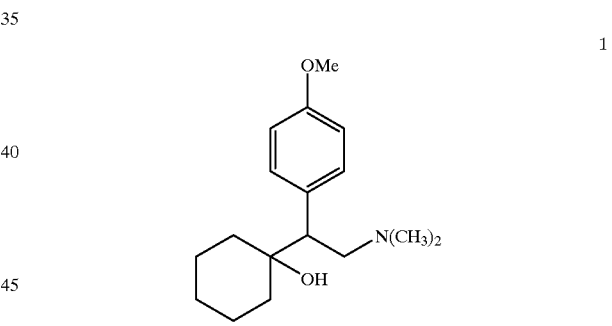

1

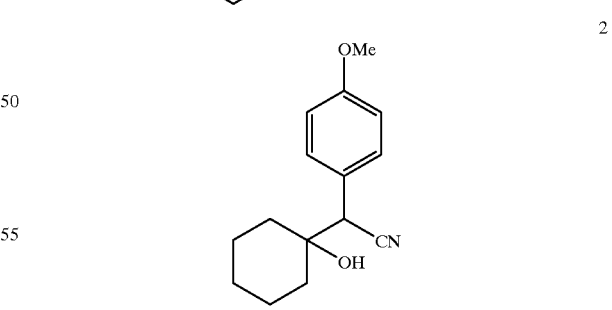

2 with a formylating agent in a protic solvent in the presence of a catalyst at a temperature in the range between 30–60° C. for a time period in the range of 6–16 hours at a pressure in the range of 100 to 400 psi of hydrogen, removing the catalyst by filtration, isolating and purifying the compound of formula 1.

In one embodiment of the invention the unreacted compound of formula 2 is recycled.

In one embodiment of the invention, the formylating agent comprises 35% formalin.

In another embodiment of the invention, the protic solvent comprises methyl alcohol.

In a further embodiment of the invention, the catalyst is Raney nickel.

In another embodiment of the present invention, the compound of formula 2 is prepared by treatment of cyclohexanone with 4-methoxy phenyl acetonitrile in the presence of base by the process described in copending patent application number 09/796,084.

In another embodiment of the present invention, the Raney nickel used is in the ratio 1:1, 2:1 and 3:1 (w/v) as that of the starting material.

In still another embodiment of the present invention, the pressure is 200 psi of hydrogen.

In yet another embodiment of the present invention the reaction time is 10 hours.

In a further embodiment of the invention, the unreacted starting material is fully recovered and recycled.

DETAILED DESCRIPTION OF THE INVENTION

The process of the present invention is described by the following examples, which are illustrative only and should not be construed as limit to the scope of the reaction in any manner.

EXAMPLE 1

To a solution of 1[Cyano (4-methoxyphenyl)methyl] cyclohexanol having formula (2) (5.0 parts, 0.02 mole) in methanol (100 parts) was added formalin (35%soln, 25 parts) and Raney nickel (5 ml, settled material). The mixture was hydrogenated under pressure (200 psi) at 60° C. for 6 hrs. The reaction was removed, filtered, the Raney nickel washed with methanol, (4×25 parts) the combined filtrates concentrated to an oily residue. It was then dissolved in ethyl acetate (100 parts) and partitioned between 10% dil HCl. The aqueous layer was washed with ethyl acetate, basified to pH 10 using 25% aqueous sodium hydroxide solution, saturated with sodium chloride and extracted with ethyl acetate, after washing with brine (2×25 parts) and drying over $Na_2SO_4$ was concentrated on rotaevaporator to get a bright white solid m.p. 74–6° C. Yield 1.6 parts (28%). The acid insoluble portion after washing and drying was concentrated to get the unreacted nitrile (3 parts, 60%). $^1$HNMR $CDCl_3$) δ(ppm): 7.32–6.98 (4H, q, p-substituted aromatic) 3.78 (3H, s, OC$\underline{H}_3$) 3.64 (2H, m, C$\underline{H}_2$ N(CH$_3$)$_2$ 3.06 (1H, m, C$\underline{H}$—CH$_2$N—(CH$_3$) 2.74 (6H, s, N(C$\underline{H}_3$)$_2$, 1.38 (10H, Br m, aliphatic cyclohexyl).

EXAMPLE 2

To a solution of 1[Cyano(4-methoxyphenyl)methyl] cyclohexanol having formula (2) (5.0 parts, 0.02 mole) in methanol (100 parts) was added formalin (35%soln, 25 parts) and Raney nickel (5 ml, settled material). The mixture was hydrogenated under pressure (200 psi) at 30° C. for 16 hrs. The reaction was removed, filtered, the Raney nickel washed with methanol, (4×25 parts) the combined filtrates concentrated to an oily residue. It was then dissolved in ethyl acetate (100 parts) and partitioned between 10% dil HCl. The aqueous layer was washed with ethyl acetate, basified to pH 10 using 25% aqueous sodium hydroxide solution, saturated with sodium chloride and extracted with ethyl acetate, after washing with brine (2×25 parts) and drying ($Na_2SO_4$) was concentrated on a rotaevaporator to get a bright white solid m.p. 74–6° C. Yield 0.85 parts (15%). The acid insoluble portion after washing and drying was concentrated to get the unreacted nitrile 2–3 parts, 60%).

EXAMPLE 3

To a solution of 1[Cyano(4-methoxyphenyl)methyl] cyclohexanol having formula (2) (5.0 parts, 0.02 mole) in methanol (100 parts) was added formalin (35%soln, 25 parts) and Raney nickel (1.25 ml, settled material). The mixture was hydrogenated under pressure (200 psi) at 60° C. for 16 hrs. The reaction was removed, filtered, the Raney nickel washed with methanol, (4×25 parts) and the combined filtrates concentrated to an oily residue. It was then dissolved in ethyl acetate (100 parts) and partitioned between 10% dil HCl. The aqueous layer was washed with ethyl acetate, basified to pH 10 using 25% aqueous sodium hydroxide solution, saturated with sodium chloride and extracted into ethyl acetate. after washing with brine (2×25 parts) and drying ($Na_2SO_4$) was concentrated on a rotaevaporator to get a bright white solid m.p. 74–6° C. Yield 0.85 parts (15%). The acid insoluble portion after washing and drying was concentrated to get the unreacted nitrile 2 (3.2 parts, 64%).

EXAMPLE 4

To a solution of 1[Cyano(4-methoxyphenyl)methyl] cyclohexanol having formula (2) (5.0 parts, 0.02 mole) in methanol (100 parts) was added formalin (35%soln, 25 parts) and Raney nickel (2.5 ml, settled material). The mixture was hydrogenated under pressure (400 psi) at 60° C. for 10 hrs. The reaction was removed, filtered, the Raney nickel washed with methanol, (4×25 parts) the combined filtrates concentrated to an oily residue. It was then dissolved in ethyl acetate (100 parts) and partitioned between 10% dil HCl. The aqueous layer was washed with ethyl acetate, basified to pH 10 using 25% aqueous sodium hydroxide solution, saturated with sodium chloride and reextracted into ethyl acetate, after washing with brine (2×25 parts) and drying ($Na_2SO_4$) was concentrated on a rotaevaporator to get a bright white solid m.p. 74–6° C. Yield 1.6 parts, 30%. The ethyl acetate portion after washing with water (2×20 parts) and drying was concentrated to get the unreacted nitrile 2 (3.2 parts, 64%)

We claim:
1. A process for the preparation of 2-[dimethylamino-(4-methoxyphenyl)ethyl]-cyclohexanol of formula 1 which comprises reducing 1-[cyano(4-methoxyphenyl)-methyl] cyclohexanol of formula 2

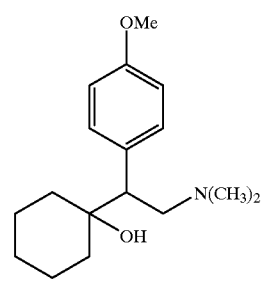

-continued

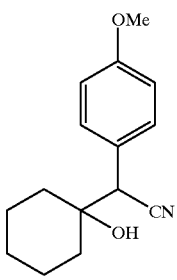

with a formylating agent in a protic solvent in the presence of a catalyst at a temperature in the range between 30–60° C. for a time period in the range of 6–16 hours at a pressure in the range of 100 to 400 psi of hydrogen, removing the catalyst by filtration, isolating and purifying the compound of formula 1.

2. A process as claimed in claim 1 wherein the formylating agent comprises 35% formalin.

3. A process as claimed in claim 1 wherein the protic solvent comprises methyl alcohol.

4. A process as claimed in claim 1 wherein the catalyst used is Raney nickel.

5. A process as claimed in claim 4 wherein the Raney nickel used is in the ratio 1:1 to 3:1 (w/v) to the starting material.

6. A process as claimed in claim 1 wherein the pressure is 200 psi of hydrogen.

7. A process as claimed in claim 1 wherein the reaction time is 10 hours.

8. A process as claimed in any preceding claim wherein the unreacted starting material is fully recovered and recycled.

* * * * *